US012161842B2

(12) United States Patent
Ulrich et al.

(10) Patent No.: US 12,161,842 B2
(45) Date of Patent: Dec. 10, 2024

(54) SYSTEM AND METHOD FOR SWITCHING BETWEEN MEDICAMENT DELIVERY CONTROL ALGORITHMS

(71) Applicant: Tandem Diabetes Care, Inc., San Diego, CA (US)

(72) Inventors: Thomas R. Ulrich, Oceanside, CA (US); Keith P. Kogler, San Diego, CA (US)

(73) Assignee: TANDEM DIABETES CARE, INC., San Diego, CA (US)

( * ) Notice: Subject to any disclaimer, the term of this patent is extended or adjusted under 35 U.S.C. 154(b) by 431 days.

(21) Appl. No.: 17/575,306

(22) Filed: Jan. 13, 2022

(65) Prior Publication Data
US 2022/0134001 A1 May 5, 2022

Related U.S. Application Data

(63) Continuation of application No. 16/598,343, filed on Oct. 10, 2019, now Pat. No. 11,224,693.
(Continued)

(51) Int. Cl.
*A61M 5/172* (2006.01)
*A61M 5/142* (2006.01)
(Continued)

(52) U.S. Cl.
CPC ...... *A61M 5/1723* (2013.01); *A61M 5/14248* (2013.01); *G16H 20/17* (2018.01);
(Continued)

(58) Field of Classification Search
CPC ............ A61M 5/1723; A61M 5/14544; A61M 5/172; A61M 5/16831; A61M 5/16804; A61M 5/142; A61M 5/145; A61M 5/16877; A61M 5/14276; A61M 5/1407; A61M 5/14; A61M 5/1413; A61M 5/14566; A61M 2005/14208; A61M 2005/14296; A61M 2005/1726; A61M 2005/1405; A61M 2005/14268; A61M 2205/52; A61M 2205/18; A61M 2205/50; A61M 2205/502; A61M 2205/8206; A61M 2205/3303; A61M 2205/35; A61M 2205/3584; A61M 2205/3334; A61M 2205/33; A61M 2205/505; A61M 2205/3592; A61M 2230/201; A61M 2230/63; A61M 2230/005; A61M 2230/00; A61M 20/17;
(Continued)

(56) References Cited

U.S. PATENT DOCUMENTS

| 2005/0065465 | A1* | 3/2005 | Lebel | A61M 5/172 |
| | | | | 604/66 |
| 2010/0204650 | A1* | 8/2010 | Hungerford | A61M 5/16804 |
| | | | | 715/781 |

(Continued)

*Primary Examiner* — Manuel A Mendez
(74) *Attorney, Agent, or Firm* — Morgan, Lewis & Bockius LLP

(57) ABSTRACT

Disclosed herein are systems and methods for safely switching between medicament delivery control algorithms for control of an ambulatory infusion pump or other medical device. Infusion pumps and/or remote control devices may be capable of operating different algorithms for delivery of medicament and provided herein are mechanisms for safely transitioning between algorithms.

20 Claims, 10 Drawing Sheets

Related U.S. Application Data

(60) Provisional application No. 62/743,901, filed on Oct. 10, 2018.

(51) Int. Cl.
*G16H 20/17* (2018.01)
*G16H 40/67* (2018.01)

(52) U.S. Cl.
CPC ......... *G16H 40/67* (2018.01); *A61M 2205/50* (2013.01); *A61M 2205/505* (2013.01); *A61M 2205/52* (2013.01); *A61M 2230/201* (2013.01)

(58) Field of Classification Search
CPC ...... A61M 20/60; A61M 20/30; A61M 20/13; A61M 19/3468; A61M 19/00
See application file for complete search history.

(56) References Cited

U.S. PATENT DOCUMENTS

| | | | |
|---|---|---|---|
| 2011/0257798 A1* | 10/2011 | Ali | G06F 11/0796 700/282 |
| 2018/0185578 A1* | 7/2018 | Monirabbasi | A61M 5/1723 |
| 2019/0231207 A1* | 8/2019 | Perschbacher | G16H 40/63 |
| 2023/0238091 A1* | 7/2023 | Gupta | A61M 5/172 604/82 |

* cited by examiner

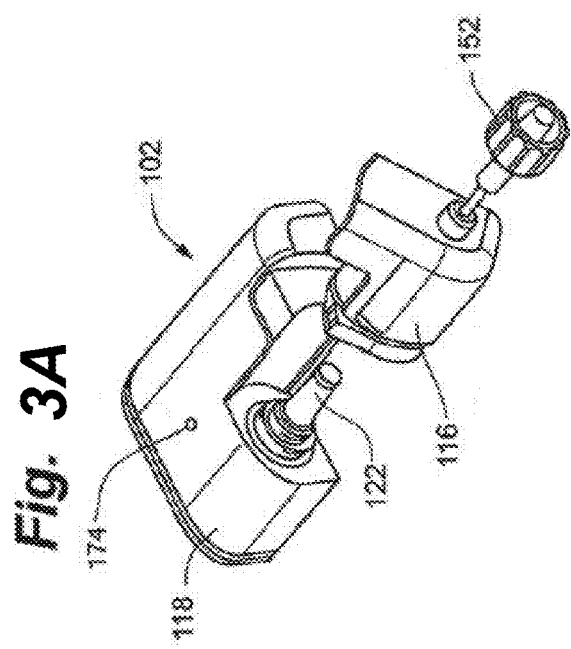
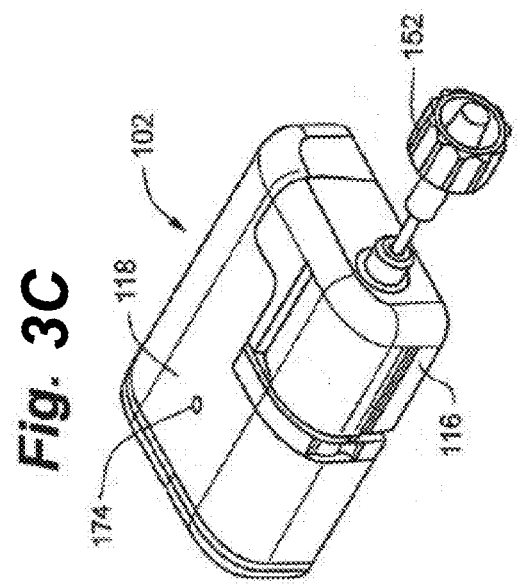
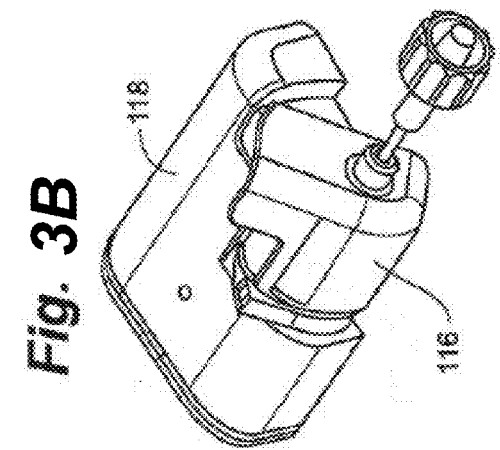

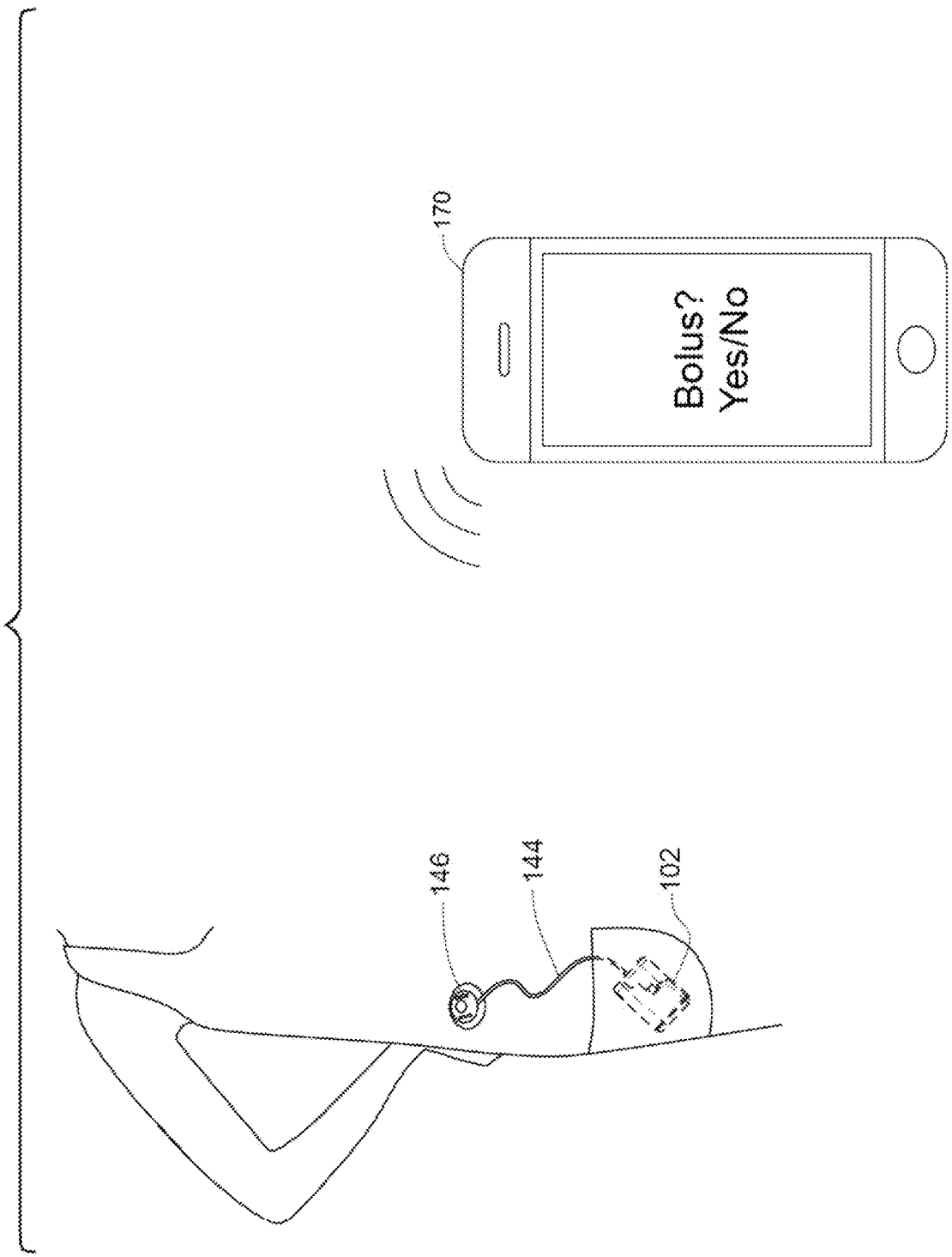

SYSTEM AND METHOD FOR SWITCHING BETWEEN MEDICAMENT DELIVERY CONTROL ALGORITHMS

RELATED APPLICATION

This application is a continuation of U.S. application Ser. No. 16/598,343 filed Oct. 10, 2019, which claims the benefit of U.S. Provisional Application No. 62/743,901 filed Oct. 10, 2018, which are hereby incorporated herein in its entirety by reference.

TECHNICAL FIELD

The present invention is directed to portable infusion pumps and more particularly algorithms for controlling portable infusion pumps.

BACKGROUND

There are a wide variety of medical treatments that include the administration of a therapeutic fluid in precise, known amounts at predetermined intervals. Devices and methods exist that are directed to the delivery of such fluids, which may be liquids or gases, are known in the art.

One category of such fluid delivery devices includes insulin injecting pumps developed for administering insulin to patients afflicted with type I, or in some cases, type II diabetes. Some insulin injecting pumps are configured as portable or ambulatory infusion devices can provide continuous subcutaneous insulin injection and/or infusion therapy as an alternative to multiple daily injections of insulin via a syringe or an insulin pen. Such pumps are worn by the user and may use replaceable cartridges. In some embodiments, these pumps may also deliver medicaments other than, or in addition to, insulin, such as glucagon, pramlintide, and the like. Examples of such pumps and various features associated therewith include those disclosed in U.S. Patent Application Publication No. 2013/0053816, U.S. Pat. Nos. 8,573,027, 8,986,253, U.S. Patent Application Publication No. 2013/0324928, U.S. Patent Application Publication No. 2013/0331790, U.S. Pat. No. 8,287,495 and U.S. patent application Ser. No. 15/158,125, each of which is hereby incorporated herein by reference in its entirety.

Ambulatory infusion pumps such as those described above are generally controlled by software algorithms running locally on an on-board processor housed within the pump. Some pumps may include one or more algorithms that can be utilized, including one or more open loop algorithms in which the user primarily programs medicament deliveries and one or more closed loop algorithms that automatically adjust medicament deliveries based on, e.g., continuous glucose monitoring (CGM) data. A user may be able to switch among these algorithms and/or the processor can be configured to automatically switch algorithms under various conditions. It is important when switching algorithms that the transition between algorithms not result in either missed medicament deliveries or double medicament deliveries with two algorithms dosing based on the same event.

In addition, with the proliferation of handheld electronic devices, such as mobile phones (e.g., smartphones), there is a desire to be able to remotely utilize such devices, as well as dedicated wireless controllers designed to work with one or more infusion pumps and/or types of infusion pumps, to optimize usage of infusion pumps. These remote controllers would enable a pump to be monitored, programmed and/or operated more privately, more conveniently and more comfortably. Accordingly, one potential use of dedicated remote devices and handheld consumer electronic devices (such as smartphones, tablets and the like) is to utilize such devices as controllers for remotely programming and/or operating infusion pumps.

Such remote control devices include internal memory, one or more processors, etc. such that those devices would be capable of independently running one or more software algorithms for control of an infusion pump alternatively or in addition to a software algorithm that may be operable on the pump itself. However, use of different software algorithms that may be provided by, e.g., a third party not affiliated with the manufacturer of the infusion pump brings risk of the algorithm not having critical patient data needed for proper therapy determinations.

SUMMARY

Disclosed herein are systems and methods for safely switching between medicament delivery control algorithms for control of an ambulatory infusion pump or other medical device. Infusion pumps and/or remote control devices may be capable of operating different algorithms for delivery of medicament and provided herein are mechanisms for safely transitioning between algorithms.

According to embodiments, a pump and/or remote control device can include multiple different control algorithms for making therapy decisions for delivery of medicament with the pump that can be user-selectable and/or automatically transitioned between by the device. Prior therapy data can be shared and/or accessed by a new control algorithm to ensure the new algorithm does not provide double doses or otherwise make dosing decisions inconsistent with prior therapy. A supervisory control algorithm can also be provided, with the supervisory control algorithm reviewing the therapy commands of the new control algorithm over a transition period to ensure a bumpless transition from the previous control algorithm to the new control algorithm.

In an embodiment, a method of providing diabetes therapy to a patient with an ambulatory infusion pump includes first delivering medicament to the patient according to a first medicament delivery control algorithm and then altering delivery of the medicament to being determined by a second medicament delivery control algorithm. Upon altering delivery of the medicament to being determined by the second medicament delivery control algorithm, a temporary third algorithm comprising a supervisory predictive low glucose suspend algorithm can be activated. The supervisory predictive low glucose suspend algorithm can review medicament delivery commands determined by the second medicament delivery control algorithm and selectively prevent or enable execution of the medicament delivery commands based on the review. The supervisory predictive low glucose suspend algorithm can be deactivated upon expiration of a transition period.

According to embodiments, a smartphone or other remote device can control a variety of infusion pump types, from a single manufacturer or multiple manufacturers, using one or more control algorithms accessed from the cloud rather than directly from the pump and/or pump manufacturer and via protocols that are standardized to interface with the communications software and equipment resident on the particular infusion pump. The pump can track all medicament delivery made with the pump and share certain therapy parameters with connected remote control algorithms in order for such remote control algorithms to have accurate data for safely making therapy determinations.

In one embodiment, an ambulatory infusion pump includes a default medicament delivery algorithm thereon that makes therapy determinations and causes the pump to provide therapy to a patient based on those determinations. During pump operation, the pump maintains a current-state-file that is continually updated to track critical data relating to the patient's therapy. The pump can selectively connect with a remote device, such as a smartphone, to be controlled by a remote medicament delivery algorithm executed on the remote device. Upon establishing a connection with a remote algorithm, the pump transfers the current-state-file to the remote device to enable the remote algorithm to utilize the data in the file to make accurate and safe therapy determinations. As the pump is controlled by the remote device, the current-state-file continues to be updated for later use by the default algorithm or a different remote device and/or remote algorithm. If the pump becomes disconnected from the remote algorithm, the pump can automatically revert back to the default algorithm.

The above summary is not intended to describe each illustrated embodiment or every implementation of the subject matter hereof. The figures and the detailed description that follow more particularly exemplify various embodiments.

BRIEF DESCRIPTION OF THE DRAWINGS

Subject matter hereof may be more completely understood in consideration of the following detailed description of various embodiments in connection with the accompanying figures, in which:

FIGS. 3A-3C depicts an embodiment of a pump system according to the disclosure.

FIG. 5 depicts an embodiment of a pump system according to the disclosure.

DETAILED DESCRIPTION OF THE DRAWINGS

The following detailed description should be read with reference to the drawings in which similar elements in different drawings are numbered the same. The drawings, which are not necessarily to scale, depict illustrative embodiments and are not intended to limit the scope of the invention.

Figure 1:
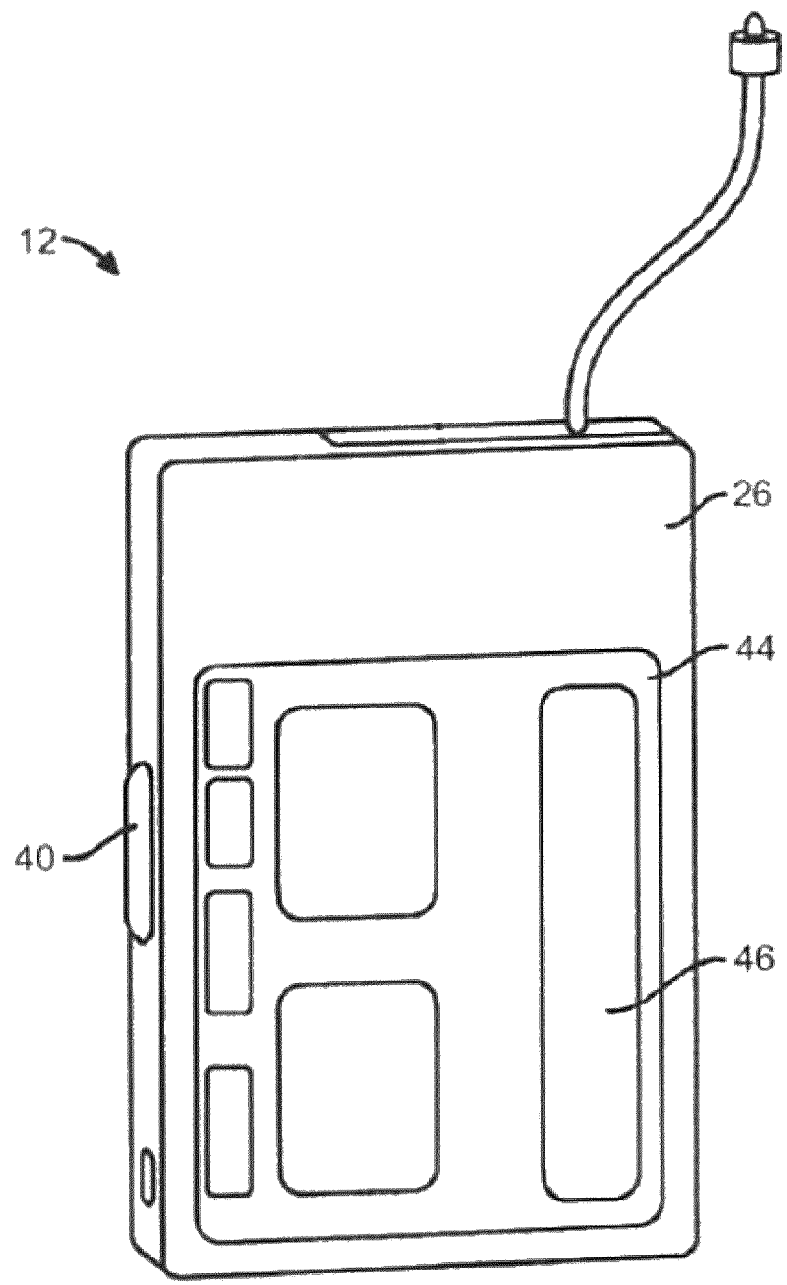
FIG. 1 depicts an embodiment of a pump system according to the disclosure.

FIG. 1 depicts an exemplary medical device that can be used with embodiments of the present invention. In this embodiment, the medical device is configured as a pump 12. Pump 12 may be an infusion pump that includes a pumping or delivery mechanism and reservoir for delivering medicament to a patient and an output/display 44. The type of output/display 44 may vary as may be useful for a particular application. The output/display 44 may include an interactive and/or touch sensitive screen 46 having an input device such as, for example, a touch screen comprising a capacitive screen or a resistive screen. The pump 12 may additionally include a keyboard, microphone, or other input device known in the art for data entry, which may be separate from the display. The pump 12 may also include a capability to operatively couple to one or more blood glucose meters (BGMs) or continuous blood glucose monitors (CGMs) and/or one or more secondary display devices such as a remote display, a remote control device, a laptop computer, personal computer, tablet computer, a mobile communication device such as a smartphone, a wearable electronic watch or electronic health or fitness monitor, or personal digital assistant (PDA), a CGM display etc.

The one or more other display devices may be configured to be used in place of output/display 44 or to work in connection with output/display 44 such that information may be repeated in exact or similar fashion between output/display 44 and one or more other displays, such that different information may be repeated between/among output/display 44 and one or more other display devices, or such that information is presented solely on one or more other display devices. Such one or more other display devices may also include the capability to allow a user to input information and/or commands for operation of the infusion pump, including, for example, via a touchscreen, microphone, keyboard or other input devices as are known in the art.

Figure 2:
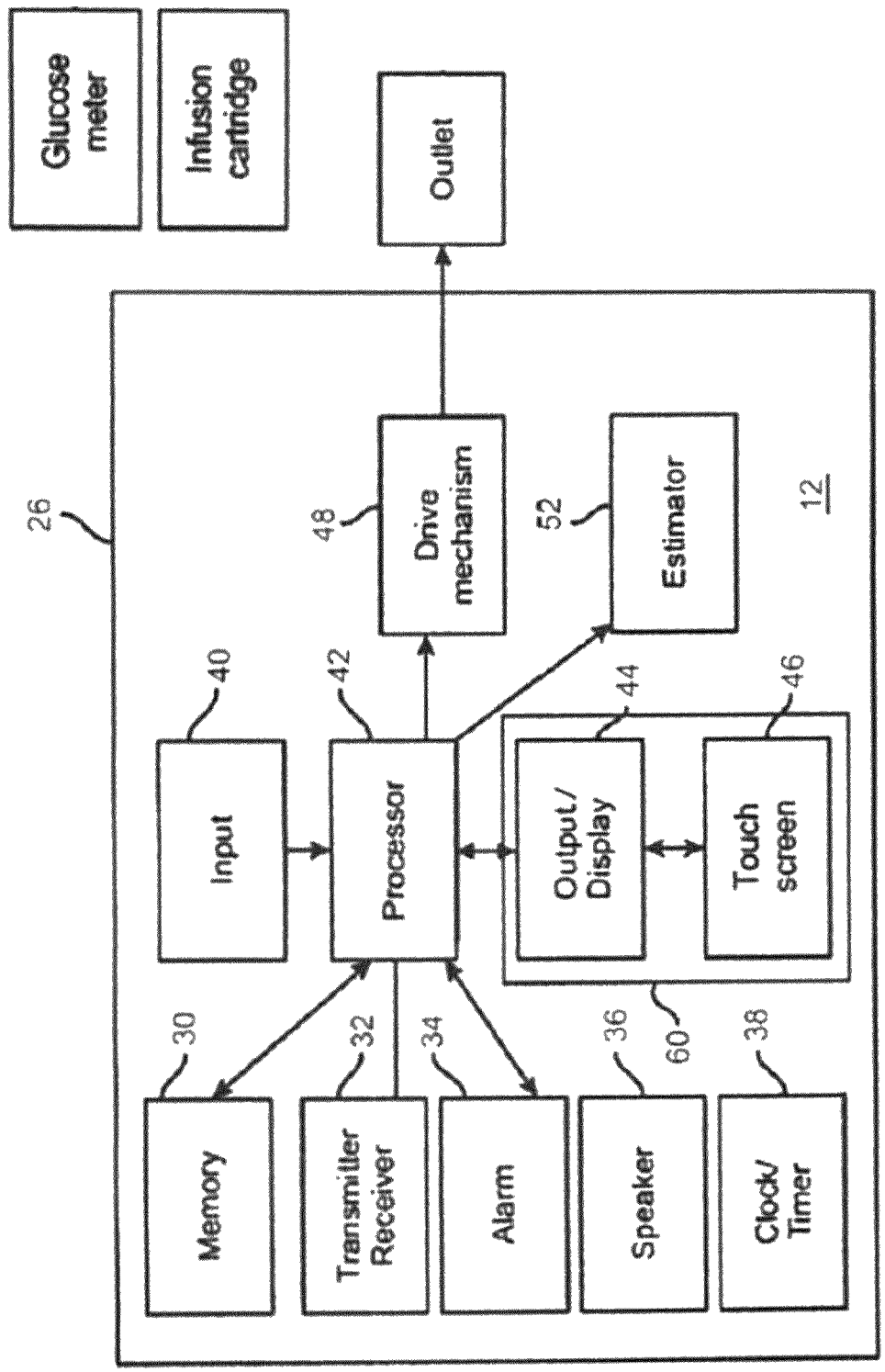
FIG. 2 depicts a block diagram representing an embodiment of a pump system according to the disclosure.

In one embodiment, the medical device can be an ambulatory pump configured to deliver insulin to a patient. Further details regarding such pump devices can be found in U.S. Pat. No. 8,287,495, which is incorporated herein by reference in its entirety. In other embodiments, the medical device can be an infusion pump configured to deliver one or more additional or other medicaments to a patient. In a further embodiment, the medical device can be a glucose meter such as a BGM or CGM. Further detail regarding such systems and definitions of related terms can be found in, e.g., U.S. Pat. Nos. 8,311,749, 7,711,402 and 7,497,827, each of which is hereby incorporated by reference herein in its entirety. FIG. 2 illustrates a block diagram of some of the features that can be used with embodiments of the invention, including features that may be incorporated within the housing 26 of a medical device such as a pump 12. The pump 12 can include a processor 42 that controls the overall functions of the device. The infusion pump 12 may also include, e.g., a memory device 30, a transmitter/receiver 32, an alarm 34, a speaker 36, a clock/timer 38, an input device 40, a user interface suitable for accepting input and commands from a user such as a caregiver or patient, a drive mechanism 48, an estimator device 52 and a microphone (not pictured). One embodiment of a user interface as shown in FIG. 2 is a graphical user interface (GUI) 60 having a touch sensitive screen 46 with input capability. In some embodiments, the processor 42 may communicate with one or more other processors within the pump 12 and/or one or more processors of other devices, for example, a continuous glucose monitor (CGM), display device, smartphone, etc. through the transmitter/receiver. The processor 42 may also include programming that may allow the processor to receive signals and/or other data from one or more input devices, such as sensors that may sense pressure, temperature and/or other parameters.

FIGS. 3A-3C depict another pump system including a pump 102 that can be used with embodiments of the invention. Drive unit 118 of pump 102 includes a drive mechanism 122 that mates with a recess in disposable cartridge 116 of pump 102 to attach the cartridge 116 to the drive unit 118 and provide for delivery of medicament such as insulin from the cartridge 116 to a user through a cannula. Further details regarding such pumps can be found in U.S. patent application Ser. No. 14/707,851 filed May 8, 2015 and U.S. Patent Publication Nos. 2016/0339172 and 2017/0049957, each of which is hereby incorporated herein by reference in its entirety.

In one embodiment, pump 102 includes a processor that controls operations of the pump and, in some embodiments, may receive commands from a separate device for control of operations of the pump. Such a separate device can include, for example, a dedicated remote control or a smartphone or other consumer electronic device executing an application configured to enable the device to transmit operating commands to the processor of pump 102. In some embodiments, the processor can also transmit information to one or more separate devices, such as information pertaining to device parameters, alarms, reminders, pump status, etc. In one embodiment, pump 102 includes a light source, such as a light emitting diode (LED) 174, that can indicate various pump information and status.

Figure 4B:
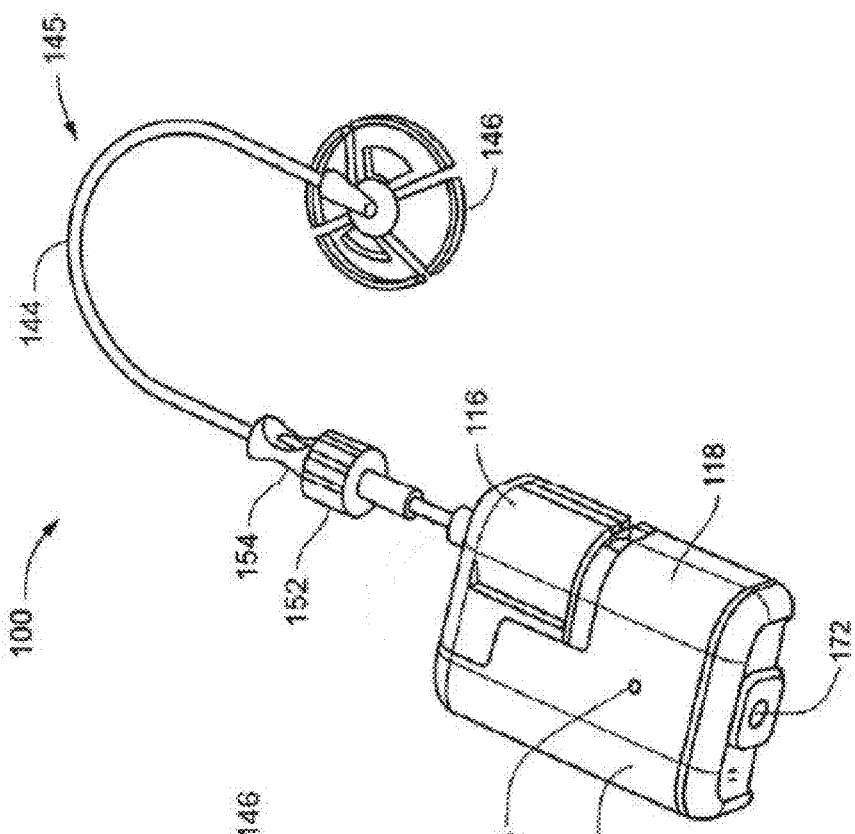
FIGS. 4A-4B depict an embodiment of a pump system according to the disclosure.
Figure 4A:
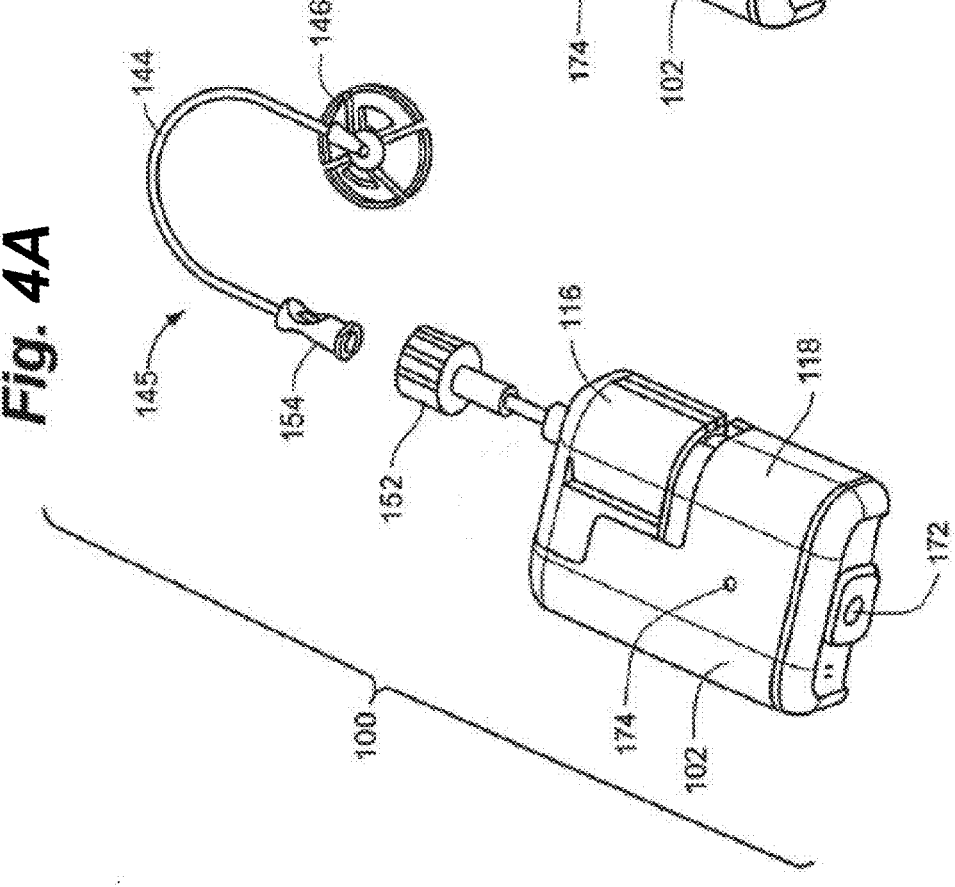

As depicted in the embodiment of FIGS. 4A-4B, pump system 100 can include a pump 102 and an infusion set 145. FIG. 4A depicts this infusion set 145 as not connected to pump while FIG. 4B depicts infusion set 145 connected to pump 102 via connectors 154 and 152. Infusion set 145 can include tubing 144 extending between a connector 154 and a site connector 146. Connector 154 can be configured to couple to pump 102 at connector 152. Site connector 146 can be configured to be attached to an infusion site on a user, while pump 102 can be carried in a separate location, such as the user's pocket (as depicted in FIG. 5) or another location on the user's body. Various lengths of tubing 144 can be used in this embodiment to accommodate the user's preference.

Figure 6B:
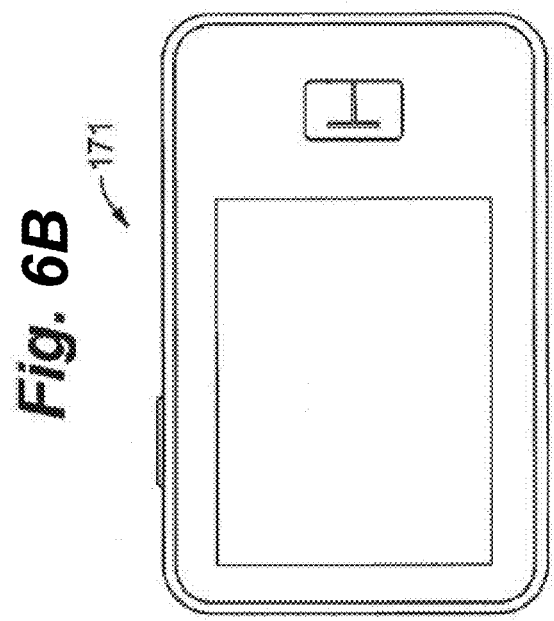
FIGS. 6A-6B depict remote control devices for a pump system according to embodiments of the disclosure.
Figure 6A:
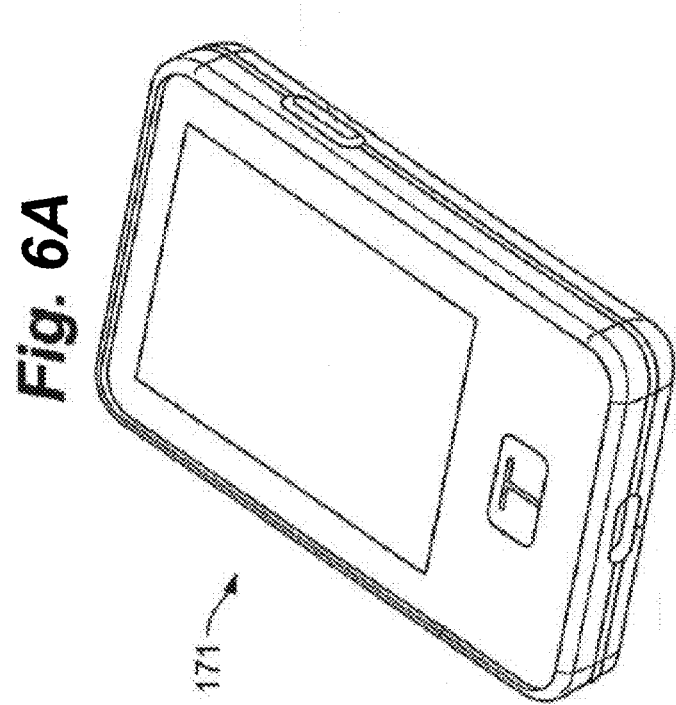

Referring to FIGS. 5-6B, one or more remote control devices 170, 171 can be used to communicate with the processor of pump 12 and/or pump 102 to control delivery of medicament and transfer data with pump via a wired or a wireless electromagnetic signal, such as via, e.g., a near field communication (NFC) radio frequency (RF) modality or other RF modalities such as Bluetooth®, Bluetooth® low energy, mobile or Wi-Fi communication protocols, for example, according to embodiments of the present disclosure. Such a remote control can include, for example, a mobile communication device 170, such as a smart phone (as depicted in FIG. 5) executing a software application for control of the pump, a dedicated remote controller 171 (as depicted in FIGS. 6A-6B), a wearable electronic watch or electronic health or fitness monitor or personal digital assistant (PDA), etc., or a tablet, laptop or personal computer. Such communications between (and among) the one or more remote control devices 170, 171 and pump 102 may be one-way or two-way for, e.g., effective transfer of data among the devices and the pump, control of pump operations, updating software on the devices and/or pump, and allowing pump-related data to be viewed on the devices and/or pump.

As noted above, some users of ambulatory infusion pumps would like to be able to individually select a software control algorithm themselves for execution by such a remote control device rather than solely employing a software control algorithm provided by the manufacturer of the infusion pump. Currently, however, use of such third party algorithms introduces additional concerns. For example, third party algorithms may not have been tested by the pump manufacturer, either for efficacy of treatment or for compatibility with a given pump and there is therefore a risk that the algorithm will not provide proper treatment. In addition, an algorithm downloaded onto the pump from a remote source may not have had prior access to patient data and could therefore initiate therapy inconsistent with the patient's recent therapy. Embodiments of the present invention provide safe and effective methods to enable a software algorithm being executed on a remote control device to take control of an infusion pump as well as to switch between various control algorithms. In embodiments, these methods can include utilizing the pump to track parameters related to patient therapy and to share such data with a remote control algorithm to enable the algorithm to have accurate data needed for proper therapy determinations.

Figure 7:
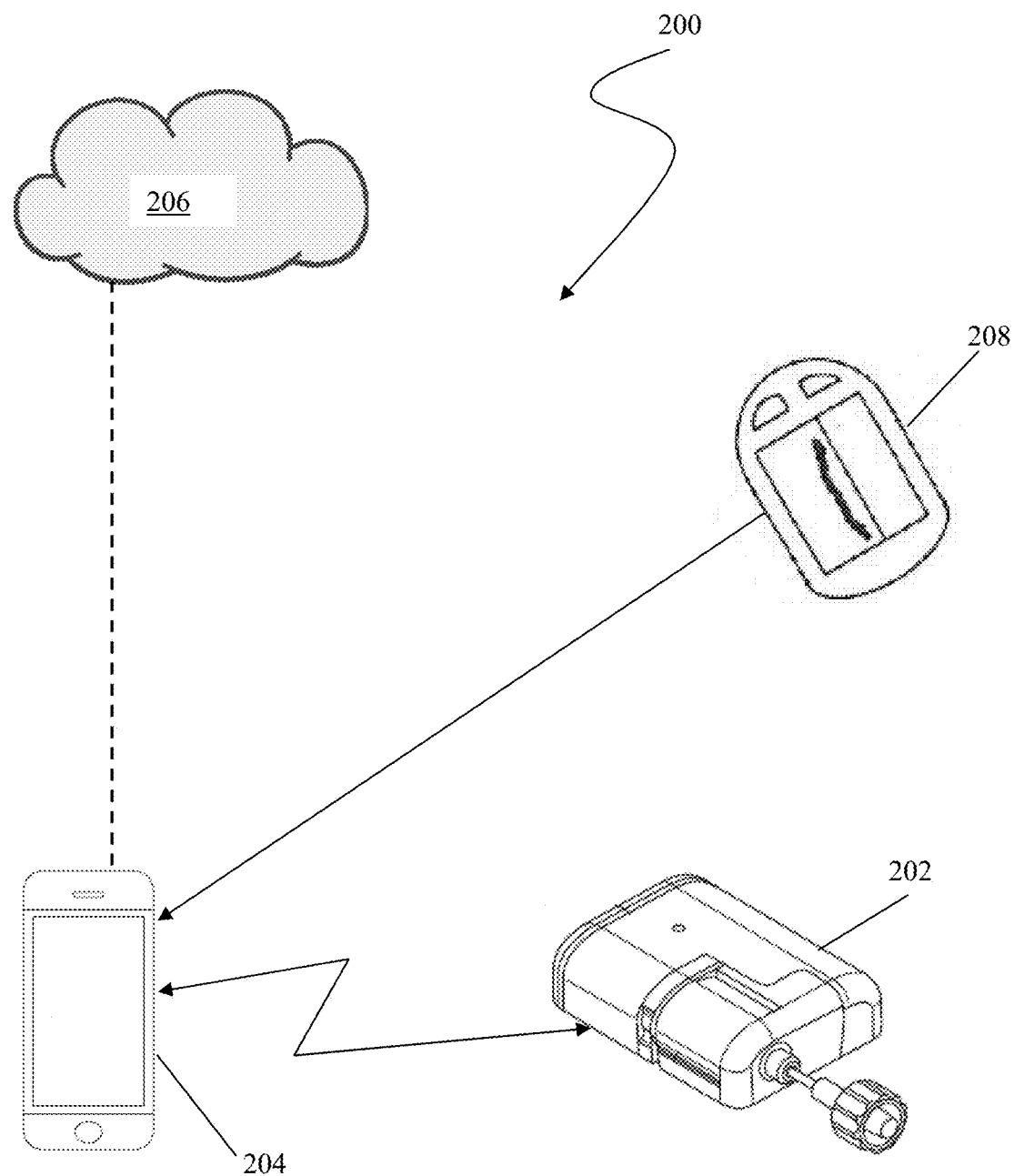
FIG. 7 depicts a system for switching between medicament delivery control algorithms according to embodiments of the disclosure.

FIG. 7 depicts various components of such a system 200 according to an embodiment. System components can include, for example, a user-wearable infusion pump 202, a remote control device 204, remote data storage 206 such as the cloud and one or more optional peripheral devices 208. In the depicted embodiment the remote control device 204 obtains data and information from the cloud, such as a medicament delivery control algorithm and communicates control commands and/or information to the infusion pump 202 and receives data and information from the infusion pump 202. Alternatively or additionally, the infusion pump 202 may communicate with the cloud 206 and the remote control device can obtain pump data through the cloud 206. As noted above, a remote control 204 can include, for example, a mobile communication device, such as a smart phone executing a software application for control of the pump, a dedicated remote controller, a wearable electronic watch or electronic health or fitness monitor or personal digital assistant (PDA), etc., or a tablet, laptop or personal computer. Optional peripheral devices, such as a continuous glucose monitor 208 and corresponding sensor, can also provide data to the remote control device 204 for use by the medicament delivery control algorithm to make therapy determinations. Such peripheral devices can alternatively or additionally include, for example, one or more of a blood glucose meter or other analyte sensing device, an activity or other health monitor, etc.

Figure 8:
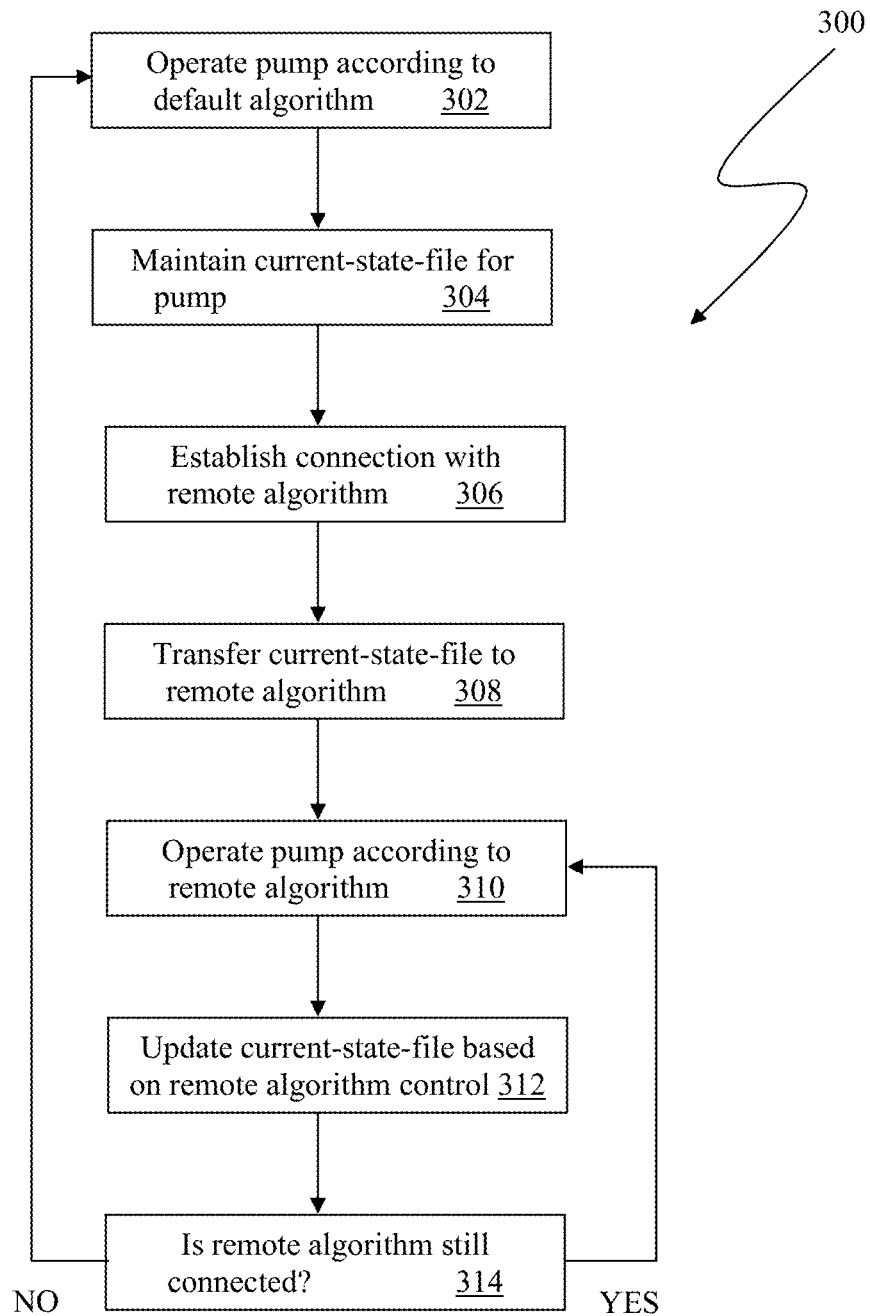
FIG. 8 depicts a flowchart of a method of switching between medicament delivery control algorithms according to embodiments of the disclosure.

FIG. 8 depicts a flowchart of an embodiment of a method 300 for safely switching between medicament delivery control algorithms. At step 302, the pump operates according to the default medicament delivery control algorithm stored on the pump that is automatically used by default whenever a remote medicament delivery control algorithm is not in use. As the pump is operated, a current-state-file for the device is continually updated at step 304. The pump is the only element of the system capable of tracking all medicament delivery made with the pump and therefore the pump must track certain parameters in order for subsequent remote control algorithms to have accurate data for safely making therapy determinations. Parameters tracked by the pump and included in the current-state-file include, for example, medicament delivery history, including bolus and basal medicament delivery history, glucose history, including data received from a CGM or BG meter, user entered BG values, etc., insulin on board, meal and exercise inputs and other patient profile settings.

At step 306, a connection is established between the pump and a remote control device seeking to control the pump with a remote medicament delivery control algorithm. The current-state-file for the pump maintained by the pump is then transferred to the remote control device at step 308 for use by the remote algorithm in making therapy determinations. This is necessary because the remote control algorithm cannot properly provide therapy to the patient without knowing parameters such as, e.g., the patient's typical basal rates, the current estimated insulin on board in the patient, etc. The pump then proceeds with being operated by the remote control device according to the remote medicament delivery control algorithm at step 310 with the pump continuing to update the current-state-file for the pump based on the therapy provided by the remote control device at step 312. The pump at step 314 continually checks to ensure that the pump is connected to the remote control device and that therapy commands are being received from the device, and, if so, the pump continues to be operated by the remote control device. If the connection is no longer present and/or no therapy commands are being received, then the pump automatically defaults back to the default on-board algorithm at step 302 using the current-state-file as updated during remote control. This could occur, for example, if the wireless connection between the devices is severed, if the user manually stops the remote control algorithm, etc. In addition, although the above method describes switching from the default on-board algorithm to a remote control algorithm, similar steps would be taken to switch from a first remote control algorithm directly to a second remote control algorithm.

With the foregoing systems and methods, a remote control device such as a smartphone can control a variety of different types of medicament infusion pumps, from a single manufacturer or multiple different manufacturers, using one or more medicament delivery control algorithms accessed from the cloud rather than directly from the pump and/or pump manufacturer. Each algorithm would be standardized to interface with the communications software, equipment and protocols of the particular infusion pump.

Although the above description relates to using multiple software algorithms for control of an infusion pump from one or more remote sources, there may be one or more available software control algorithms resident on the pump itself (or on a remote control device) that the user may be able to switch among and/or the processor may automatically switch among under various conditions. As such, a current-state-file including various parameters relating to medicament delivery with a first algorithm can be shared with and/or accessed by a second algorithm in order to ensure safe switching between algorithms operable on such a device, similar to the method described with respect to FIG. 8.

In addition, embodiments of the invention can provide additional safeguards when switching between control algorithms. Different control algorithms may calculate doses based on different factors, which can be problematic when transitioning between algorithms. For example, a first control algorithm may incorporate logic to predict future glucose levels and dose medicament based on those predictions whereas a second control algorithm may only dose based on current CGM glucose level readings. In such a situation, a user may consume a meal while operating the first algorithm and the algorithm may then deliver increased amounts of medicament (e.g., 5 units) based on a prediction that the user's glucose levels will be too high in the future due to the meal. If the user then switches to the second algorithm, the second algorithm may see the current glucose levels rise following consumption of the meal—without knowing that the first algorithm delivered a dose that is yet to take effect—and deliver a dose based on the current glucose level (e.g., 4 units). The net result may be that the user is dosed twice for the same event and receives nearly double the medicament (e.g., 9 units instead of 5 units) because the control algorithm was changed mid-therapy. Thus, changing control algorithms—whether between control algorithms already stored on a single device or between different remotely obtained control algorithms—can cause unintended side effects, such as the above example where the user is double-dosed for a single event.

Embodiments described herein can therefore employ additional control logic for managing the transition between control algorithms in addition to the control algorithm logic in order to ensure a smooth or "bumpless" transition between control algorithms. In embodiments, the transition control logic can be managed in two distinct and complementary ways. First, the therapy state of the previous control law, i.e., the current-state-file as described above, is passed over to and/or access by the new control law as the new control algorithm initiates control of the therapy. In the above-described example that resulted in double dosing, the current-state-file would indicate to the new control algorithm that the current condition relating to a rise in blood glucose from a meal had already been addressed with an increased dose. Second, the transition control logic can employ an additional predictive low glucose suspend (PLGS) feature that supervises the transition over a transition period of time. The supervising PLGS feature has the option of negating any command from the new control algorithm to dose medicament over the transition period if the glucose level of the user is trending low and the PLGS feature predicts that the glucose level will fall below a low threshold in the future (e.g., within 30 minutes). In this embodiment, the supervisory feature relates only to low glucose levels such that the new control algorithm would be free to reduce insulin as necessary as determined by the algorithm and dosing increase commands issued at higher and/or increasing glucose levels that do not implicate the low threshold would not be negated.

In an embodiment, the transition period over which the PLGS feature supervises the dosing decisions of the new control algorithm is a predetermined time period, such as, for example one hour. In other embodiments, the transition period can be based on the performance of the new control algorithm. For example, the PLGS feature may track a stability of glucose levels of the user after the new control algorithm takes control of therapy and may continue to supervise the algorithm until glucose levels meet predefined stability criteria. Such criteria can include, for example, maintaining the glucose levels within a predetermined range for a predetermined period of time.

Figure 9:
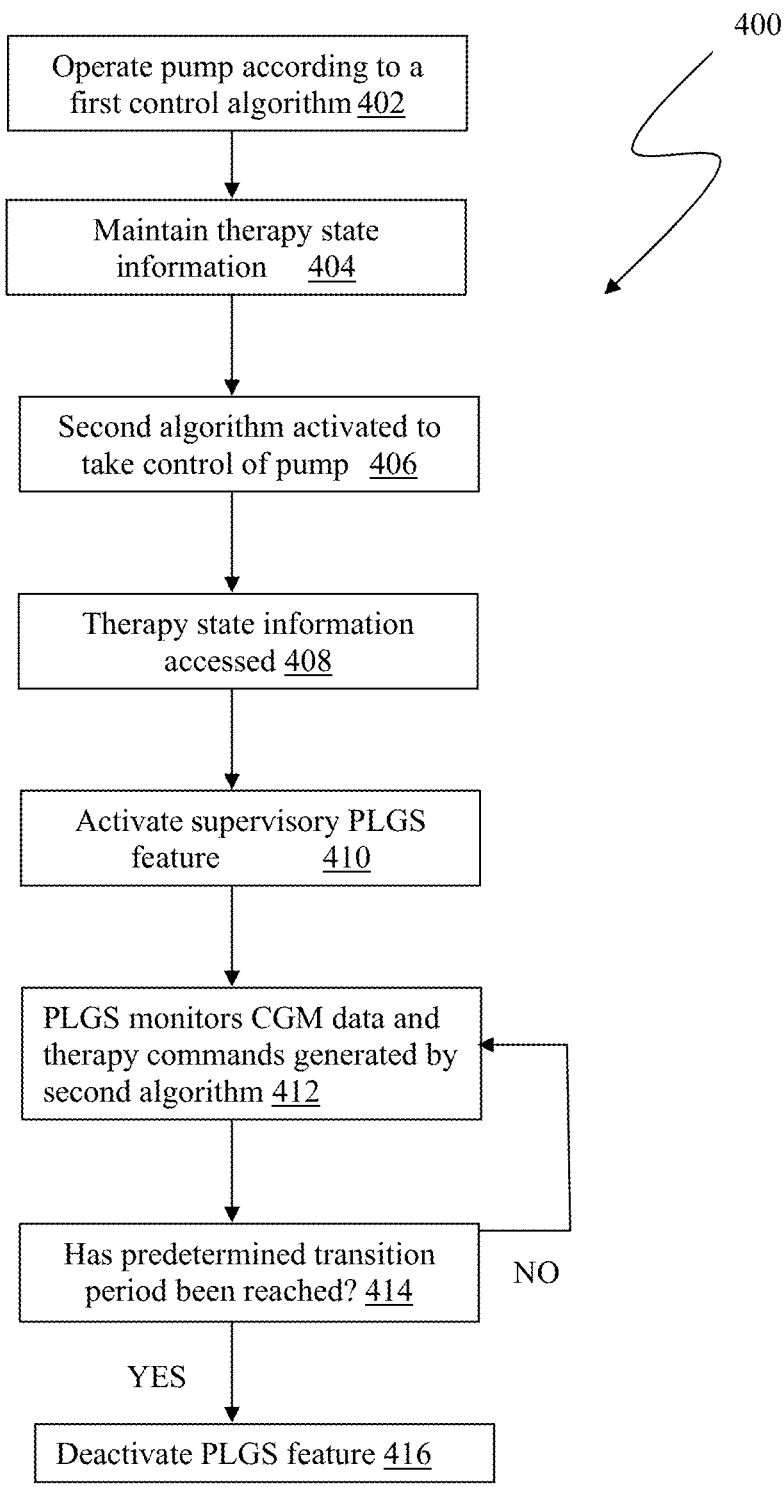
FIG. 9 depicts a flowchart of a method of switching between medicament delivery control algorithms according to embodiments of the disclosure.

FIG. 9 depicts a flow chart of a method 400 for safely switching between medicament delivery control algorithms according to an embodiment. At step 402, the pump is operated according to a first control algorithm. In an embodiment, the first control algorithm is one of a plurality of control algorithms stored on and/or accessible by the pump and/or with access to the pump. At step 404, therapy state information is maintained by the pump while therapy is determined by the first control algorithm. Pump control is switched to a second control algorithm at step 406. In various embodiments, the second control algorithm can be selected by the user or automatically switched to by the processor based on certain predetermined events or criteria.

When the system is switched to control by the second control algorithm at step 406, both steps 408 and 410 can be carried out. In step 408, the second algorithm is provided with and/or accesses the therapy state information, which can include, for example, recent therapy determinations made by the first control algorithm such as decisions to increase or decrease delivery of medicament. A supervisory PLGS feature can also be activated when the second algorithm is selected at step 410. As noted above, at step 412 the PLGS feature can be an algorithm that monitors CGM data and therapy commands generated by the second control algorithm over a transition period. The PLGS feature can generally enable commands that decrease the amount of insulin delivered and will only negate commands to increase the amount of insulin if it is determined from the CGM data that the user's glucose level is likely to go below a low glucose threshold in the near future. The PLGS feature supervises the second control algorithm until the end of the transition period is reached at step 414. In embodiments, the transition period can be a predefined amount of time or can be based on other data, such as, for example, a measure of stability of the user's glucose levels while therapy is under control of the second algorithm. Once the end of the transition period is reached, the PLGS feature can be disabled at step 416 and the second algorithm can continue controlling therapy without the supervisory feature.

Figure 10:
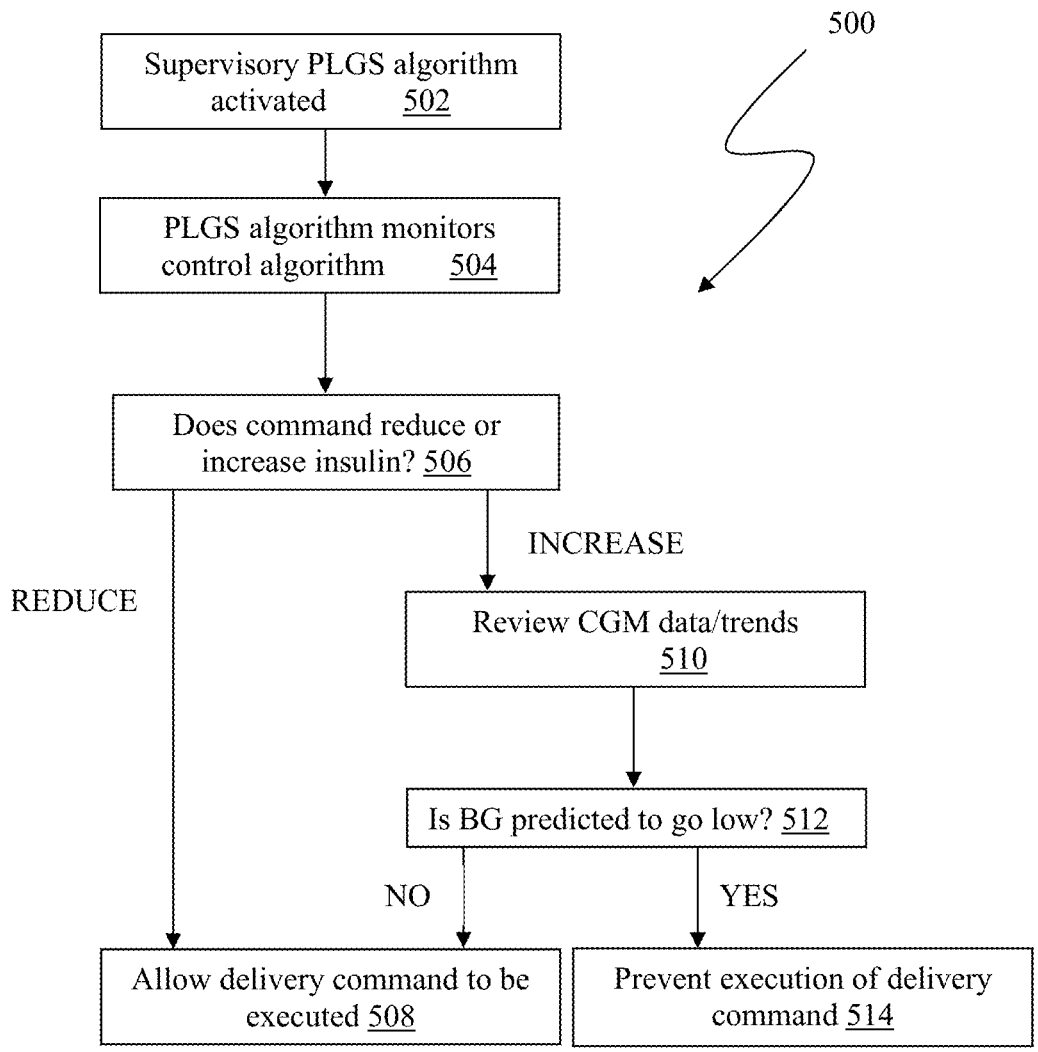
FIG. 10 depicts a flowchart of a supervisory PLGS algorithm according to embodiments of the disclosure While various embodiments are amenable to various modifications and alternative forms, specifics thereof have been shown by way of example in the drawings and will be described in detail. It should be understood, however, that the intention is not to limit the claimed inventions to the particular embodiments described. On the contrary, the intention is to cover all modifications, equivalents, and alternatives falling within the spirit and scope of the subject matter as defined by the claims.

Referring now to FIG. 10, a flowchart of a method 500 of operation of a supervisory PLGS feature according to an embodiment in the context of delivery of insulin is depicted. At step 502 the supervisory PLGS algorithm is activated. As noted above, this can be done in response to the system switching from one therapy control algorithm to another therapy control algorithm. The supervisory PLGS algorithm can reside on the device, e.g., a pump, and be activated and deactivated as needed. Upon activation, at step 504 the supervisory PLGS algorithm is superimposed onto the therapy control algorithm to monitor insulin delivery commands calculated by the control algorithm. The delivery commands are first reviewed at step 506 to determine if they reduce or increase the amount of insulin being delivered to the user. If it is determined that the delivery command reduces the amount of insulin being delivered, the command is allowed to be executed at step 508, because the PLGS feature is provided only to supervise and prevent potential low blood glucose levels and reduction of insulin is intended to raise blood glucose levels. In other embodiments, the supervisory PLGS feature can be adapted for use with other medicaments alternatively or in addition to insulin. In such cases, any medicament delivery adjustment, or combination of medicaments, intended to raise blood glucose levels would be allowed to be executed.

If the command reviewed at step 506 is one that increases insulin delivery, the PLGS algorithm reviews the user's recent CGM data and/or CGM trends at step 510 to determine if the command is permissible. To determine if the command is permissible, the PLGS algorithm determines if the user's blood glucose level is predicted to go below a low threshold at step 512.

If the user's blood glucose level is predicted to go low, the PLGS algorithm intervenes in the control algorithm to negate and prevent the delivery of the therapy command at step 514. If the user's blood glucose level is not predicted to go low, the PLGS algorithm allows the command to be executed. The determination that the user's blood glucose level is predicted to go low can be based on various different information and determined in various different manners. Information reviewed can include, for example, one or more of CGM glucose levels, CGM trends, blood glucose values entered by the user, predicted future glucose levels, past and scheduled insulin delivery, the insulin delivery command currently under review, etc. In one embodiment, the PLGS algorithm determines from CGM trends whether or not the user's glucose level will be below a low threshold a predetermined time, e.g., 30 minutes, in the future.

In a further embodiment, a supervisory PLGS feature such as described herein could be employed any time a remotely obtained, third-party algorithm such as those described above is employed. This would provide an additional safety feature with regard to third party algorithms to ensure these algorithms can run interrupted without violating the safety conditions governed by the PLGS feature.

Although the embodiments herein have been specifically described with respect to an ambulatory infusion pump, the inventions disclosed herein could be employed with any other type of programmable medical device capable of receiving and executing remote commands. Such devices include, for example, implantable pumps, defibrillators, spinal cord stimulation systems, etc. Embodiments could further include non-medical applications.

Although the infusion pump embodiments herein are specifically described primarily with respect to the delivery of insulin, delivery of other medicaments, singly or in combination with one another or with insulin, including, for example, glucagon, pramlintide, etc., as well as other applications are also contemplated. Device and method embodiments discussed herein may be used for pain medication, chemotherapy, iron chelation, immunoglobulin treatment, dextrose or saline IV delivery, treatment of various conditions including, e.g., pulmonary hypertension, or any other suitable indication or application. Non-medical applications are also contemplated.

Also incorporated herein by reference in their entirety are commonly owned U.S. Pat. Nos. 6,999,854; 8,133,197; 8,287,495; 8,408,421 8,448,824; 8,573,027; 8,650,937; 8,986,523; 9,173,998; 9,180,242; 9,180,243; 9,238,100; 9,242,043; 9,335,910; 9,381,271; 9,421,329; 9,486,171; 9,486,571; 9,492,608; 9,503,526; 9,555,186; 9,565,718; 9,603,995; 9,669,160; 9,715,327; 9,737,656; 9,750,871; 9,867,937; 9,867,953; 9,940,441; 9,993,595; 10,016,561; 10,201,656; 10,279,105; 10,279,106; 10,279,107; 10,357,603; and 10,357,606 commonly owned U.S. Patent Publication Nos. 2009/0287180; 2012/0123230; 2013/0053816; 2014/0276420; 2014/0276423; 2014/0276569; 2014/0276570; 2016/0082188; 2017/0142658; 2017/0182248; 2017/0250971; 2018/0021514; 2018/0071454; 2019/0240398; and 2019/0307952 and commonly owned U.S. patent application Ser. Nos. 16/423,675 and 16/507,146.

Further incorporated by reference herein in their entirety are U.S. Pat. Nos. 8,601,465; 8,502,662; 8,452,953; 8,451,230; 8,449,523; 8,444,595; 8,343,092; 8,285,328; 8,126,728; 8,117,481; 8,095,123; 7,999,674; 7,819,843; 7,782,192; 7,109,878; 6,997,920; 6,979,326; 6,936,029; 6,872,200; 6,813,519; 6,641,533; 6,554,798; 6,551,276; 6,295,506; and 5,665,065.

Various embodiments of systems, devices, and methods have been described herein. These embodiments are given only by way of example and are not intended to limit the scope of the claimed inventions. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the claimed inventions.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of 35 U.S.C. § 112(f) are not to be invoked unless the specific terms "means for" or "step for" are recited in a claim.

The invention claimed is:

1. An ambulatory infusion pump system, comprising:
an ambulatory infusion pump configured to deliver medicament to a patient;
a processor configured to determine medicament delivery commands for delivering medicament to the patient with the ambulatory infusion pump, wherein the processor is configured to:
determine the medicament delivery commands according to a first medicament delivery control algorithm;
determine that the medicament delivery commands should transition from being determined according to the first medicament delivery control algorithm to being determined by a second medicament delivery control algorithm;
activate a temporary supervisory algorithm configured to review and selectively prevent or enable the medicament delivery commands determined according to the second medicament delivery control algorithm for a transition period of time following the transition; and
deactivate the temporary supervisory algorithm upon expiration of the transition period of time.

2. The ambulatory infusion pump system of claim 1, wherein the processor is configured to selectively prevent or enable execution of the medicament delivery commands determined according to the second medicament delivery control algorithm by:
enabling execution of medicament delivery commands that would increase a blood glucose level of the patient; and
preventing execution of medicament delivery commands that would reduce a blood glucose level of the patient when it is predicted by the temporary supervisory algorithm that the blood glucose level of the patient is likely to drop below a low glucose threshold.

3. The ambulatory infusion pump system of claim 2, wherein the processor is configured to selectively prevent or enable execution of the medicament delivery commands determined according to the second medicament delivery control algorithm by enabling execution of medicament delivery commands that would reduce a blood glucose level of the patient when it is predicted by the temporary supervisory algorithm that the blood glucose level of the patient is not likely to drop below the low glucose threshold.

4. The ambulatory infusion pump system of claim 1, wherein the temporary supervisory algorithm is configured to selectively prevent or enable execution of the medicament delivery commands determined by the second medicament delivery control algorithm based on the review of the medicament delivery commands and on data obtained from a continuous glucose monitor.

5. The ambulatory infusion pump system of claim 4, wherein the processor is configured to review glucose level trends of the patient based on the data obtained from the continuous glucose monitor and to predict future glucose levels based on the glucose level trends.

6. The ambulatory infusion pump system of claim 1, where the processor is configured to determine that the medicament delivery commands should transition from being determined according to the first medicament delivery control algorithm to being determined by the second medicament delivery control algorithm based on patient input.

7. The ambulatory infusion pump system of claim 1, where the processor is configured to automatically determine that the medicament delivery commands should transition from being determined according to the first medicament delivery control algorithm to being determined by the second medicament delivery control algorithm based on occurrence of a predetermined event.

8. The ambulatory infusion pump system of claim 1, wherein the processor is part of the ambulatory infusion pump.

9. The ambulatory infusion pump of claim 1, further comprising a remote control device and wherein the processor is part of the remote control device.

10. The ambulatory infusion pump of claim 1, wherein the processor is further configured to store pump parameters relating to delivery of medicament with the first medicament delivery control algorithm and to utilize the stored pump parameters in determining delivery of medicament with the second medicament delivery control algorithm.

11. An ambulatory infusion pump system, comprising:
an ambulatory infusion pump configured to deliver medicament to a patient;
a memory;
a processor configured to determine medicament delivery commands for delivering medicament to the patient with the ambulatory infusion pump, wherein the processor is configured to:

cause medicament to be delivered to the patient with the ambulatory infusion pump according to a first medicament delivery algorithm;

monitor pump parameters while delivering medicament according to the first medicament delivery algorithm;

store the monitored pump parameters while medicament is delivered according to the first medicament delivery algorithm in a current state file in the memory;

establish a connection with a second medicament delivery algorithm for replacing the first medicament delivery algorithm for determining medicament to be delivered to the patient with the ambulatory infusion pump;

transfer the current state file from memory for use by the second medicament delivery algorithm; and enable medicament to be delivered according to the second medicament delivery algorithm after transferring the current state file.

12. The system of claim 11, wherein the memory and the processor are part of the ambulatory infusion pump and the first medicament delivery algorithm is a default medicament delivery control algorithm stored on the ambulatory infusion pump.

13. The system of claim 12, wherein the processor is configured to automatically revert to the default medicament delivery control algorithm if the connection with the second medicament delivery algorithm is disconnected.

14. The system of claim 12, wherein the second medicament delivery algorithm is stored in the memory of the pump.

15. The system of claim 14, further comprising receiving patient input instructing the processor to switch from the first medicament delivery algorithm to the second medicament delivery algorithm.

16. The system of claim 11, further comprising:
monitoring pump parameters while delivering medicament according to the second medicament delivery algorithm; and updating the current state file in the memory with the monitored pump parameters while delivering medicament according to the second medicament delivery algorithm.

17. The system of claim 16, further comprising:
establishing a connection with a third medicament delivery algorithm for replacing the second medicament delivery algorithm for determining medicament to be delivered to the patient with the ambulatory infusion pump;

transferring the current state file from memory for use by the third medicament delivery algorithm; and enabling medicament to be delivered according to the third medicament delivery algorithm after transferring the current state file for use by the third medicament delivery algorithm.

18. The system of claim 11, further comprising a remote control device and wherein establishing a connection with the second medicament delivery algorithm includes establishing a connection between the ambulatory infusion pump and the remote control device and transferring the current state file includes transferring the current state file from the ambulatory infusion pump to the remote control device.

19. The system of claim 18, wherein the second medicament delivery algorithm is downloaded onto the remote control device from an entity other than a manufacturer of the ambulatory infusion pump.

20. The system of claim 11, wherein the parameters stored in the current state file include one or more of medicament delivery history, glucose history and insulin on board.

* * * * *